United States Patent
Acciai et al.

(10) Patent No.: US 6,193,829 B1
(45) Date of Patent: Feb. 27, 2001

(54) METHOD AND TOOLING FOR FORMING A STENT

(75) Inventors: Michael A. Acciai, Newark Valley; Richard R. Hall, Endwell; John T. Legg, Glen Aubrey, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/226,726

(22) Filed: Jan. 7, 1999

Related U.S. Application Data (62) Division of application No. 09/025,514, filed on Feb. 18, 1998.

(51) Int. Cl.⁷ .................................. D04H 3/14; A61F 2/06
(52) U.S. Cl. .................... 156/180; 156/166; 156/433; 623/1.11; 623/1.15; 606/192; 606/194
(58) Field of Search ...................... 156/166, 180, 156/245, 433; 623/1.11, 1.12, 1.13, 1.14, 1.15, 1.16, 1.22; 606/192, 194, 195; 264/645

(56) References Cited

U.S. PATENT DOCUMENTS

| | | |
|---|---|---|
| 4,137,354 * | 1/1979 | Mayes et al. .................... 428/116 |
| 4,656,860 | 4/1987 | Orthuber et al. . |
| 5,015,253 | 5/1991 | Mac Gregor . |
| 5,019,090 | 5/1991 | Pinchuk . |
| 5,104,404 | 4/1992 | Wolff . |
| 5,135,536 | 8/1992 | Hillstead . |
| 5,170,654 | 12/1992 | Anagnostopoulos . |
| 5,217,483 | 6/1993 | Tower . |
| 5,304,200 | 4/1994 | Spaulding . |
| 5,314,472 | 5/1994 | Fontaine . |
| 5,342,348 | 8/1994 | Kaplan . |
| 5,370,683 | 12/1994 | Fontaine . |
| 5,382,261 | 1/1995 | Palmaz . |
| 5,383,892 | 1/1995 | Cardon et al. . |
| 5,405,377 | 4/1995 | Cragg . |
| 5,443,496 | 8/1995 | Schwartz et al. . |
| 5,476,508 | 12/1995 | Amstrup . |
| 5,527,354 | 6/1996 | Fontaine et al. . |
| 5,549,663 | 8/1996 | Cottone, Jr. . |
| 5,591,198 | 1/1997 | Boyle et al. . |
| 5,609,627 | 3/1997 | Goicoecheo et al. . |
| 5,618,301 | 4/1997 | Hauenstein et al. . |
| 5,624,411 | 4/1997 | Tuch . |
| 5,629,077 | 5/1997 | Turnlund et al. . |
| 5,630,829 * | 5/1997 | Lauterjung ........................... 606/198 |
| 5,716,396 | 2/1998 | Williams, Jr. . |
| 5,733,326 | 3/1998 | Tomonto et al. . |

* cited by examiner

Primary Examiner—Michael W. Ball
Assistant Examiner—Jessica Rossi
(74) Attorney, Agent, or Firm—Schmeiser, Olsen & Watts; Lawrence R. Fraley (57) ABSTRACT

The present invention relates to a method and tooling for forming a stent and the stent so formed. The stent includes filaments of a first material and joints of a second material. The present invention also discloses the above described stent in combination with an angioplasty balloon. The tooling in accordance with the present invention provides a fixture having grooves that receive the filaments of the stent to hold the filaments in place for joining. The joining of all of the filaments can be performed simultaneously by laser welding or injection molding a joint material. The tooling in accordance with the present invention also provides the capability to mold the stent as one piece. The method in accordance with the present invention includes the steps of providing a fixture with internal grooves, placing filaments into the grooves and joining the filaments together. The method also includes providing a mold having internal grooves, and injecting a molten material into the mold to fill the grooves so as to create a one-piece stent of polymer and/or metallic materials.

6 Claims, 7 Drawing Sheets

METHOD AND TOOLING FOR FORMING A STENT

This application is a divisional of application Ser. No. 09/025,514, filed on Feb. 18, 1998, currently pending. The entire disclosure of that prior application is considered as being part of the disclosure of this application and is hereby incorporated by reference herein.

BACKGROUND OF THE INVENTION

1. Technical Field

The present invention, generally, relates to endoprosthesis, and more particularly, it relates to a new stent, a stent in combination with an angioplasty balloon, tooling for forming a stent, and a method of fabricating a stent.

2. Related Art

Stents are devices used to support the walls of weak arteries and are particularly useful in the medical field of angioplasty involving the reconstruction of vessels that carry blood in both humans and animals. The stent is used to maintain such blood vessels, structurally, in a clear and open condition. Most arterial stents are formed from thin wire, e.g., 0.005 inch diameter wire. Stents are often made from inert metals such as stainless steel or tantalum. However, plastic stents are available and provide more flexibility. Unfortunately, plastic stents also lack sufficient radial stiffness for artery wall support.

For a stent to achieve maximum usefulness, it must be flexible in a bending mode during insertion, and it must exhibit stiffness in both torsional and cylindrical modes in order to provide support. The stents today are formed into the required configuration to permit a high level of plastic deformation to be achieved during their use. During use, an angioplasty balloon may be inserted into a stent which is then plastically compressed around the balloon. This assembly is inserted into a patient's blood vessel, usually an artery, and moved into position. The balloon is inflated to enlarge the stent to a desired diameter, after which the balloon is removed.

The stent, within an artery, or within any other type of vessel, is exposed to repetitive flexing as a part of a circulatory system, both from the systolic and the diastolic variations in blood pressure and from variations in movement of a body.

One method of stent fabrication today continuously feeds a wire from a spool to be formed into a generally sinusoidal configuration. Then, the wire in this sinusoidal configuration is wound around a mandrel in order to produce a helical arrangement. Next, the crests and troughs in the helical arrangement are aligned so that they touch at points, and then crests and troughs are welded at the points to provide the required supporting structure. The above described steps, however, in conjunction with the heating and cooling encountered during welding, create an undesirable work-hardening in the wire. This work hardening lowers much of the wire's ability to provide support in use. Additionally, loading and unloading of a metallic stent during use produces further fatigue of the metal, causing premature failure of support.

An additional disadvantage of present fabrication methods is that the deformation of the wire into a desired position is also relatively imprecise such that a uniformly shaped stent is difficult to create. Further, since each joint is welded individually, inconsistency of structure can be created. As a result, the stents so fabricated also lack in consistency of torsional and radial stiffness. The need to deform the wire into a given position and then join the wire also involves very high costs.

Examples of related art, which are hereby incorporated by reference, are:

U.S. Pat. No. 5,370,683 to Fontaine and assigned to Cook, Inc. describes a stent formed of a single filament wrapped around a mandrel with a series of U-shaped bends.

U.S. Pat. No. 5,304,200 to Spaulding and assigned to Cordis Corp. describes a method of making stents involving winding an elongated strand forming a helix like structure with the ends welded to an adjacent section.

U.S. Pat. No. 5,217,483 to Tower and assigned to Numed, Inc. describes a stent arranged to have U-shaped sections formed in a continuous wire with two ends and with the ends attached together to prevent axial expansion.

U.S. Pat. No. 5,549,663 to Cottone, Jr. and assigned to Cordis Corp. describes a stent formed by wrapping a wire around a mandrel and joining the filaments by welding.

U.S. Pat. No. 5,629,077 to Turulund et al. and assigned to Advanced Cardiovascular Systems, Inc. describes a stent made completely of biodegradable material.

U.S. Pat. No. 5,630,829 to Lauterjung and assigned to InterVascular, Inc. describes a stent in which adjacent stents may be connected to one another by welding at least one opposed pair of cusps together.

Accordingly, there is a need for a stent which consistently exhibits flexibility during insertion, and stiffness with a high level of plastic deformation in both torsional and radial modes to provide support during use. Further, there is a need for a stent fabrication process and tooling which creates the above described stent more easily than conventional methods and without the problem of work hardening and high cost.

SUMMARY OF THE INVENTION

The present invention is a method and tooling for forming a stent and the stent so formed. In one general aspect in accordance with the present-invention is provided a stent including at least one filament made of a first material, and joints made of a second material connecting selected filaments to one another. This aspect allows for consistent flexibility during insertion, stiffness and a high level of plastic deformation to provide support during use. The present invention also includes the above described stent in combination with an angioplasty balloon.

In a second general aspect in accordance with the present invention is provided tooling for forming a stent comprising a first part having grooves for aligning the filaments of the stent to hold the filaments in place for joining. In a third general aspect of the present invention is provided tooling for forming a stent including a device for positioning filaments and a device for joining filaments. The above two aspects allow the joining of all of the filaments to be performed simultaneously by laser welding or injection molding a joint material such as a polymer or metal. As a result, repetitive welds and deformations are alleviated, the manufacturing process is quicker, and joints of the stent are more consistently aligned. The tooling in accordance with the present invention also provides the capability to mold the stent as one piece.

In a fourth general aspect in accordance with the present invention is provided a method that eliminates repetitive welds and bending by: providing a-fixture with internal grooves, placing filaments into the grooves and joining the filaments together. The method reduces the repetitive bending and welding of the related art devices. Further, the method provides enhanced alignment of joints of the filament material, eliminates the need for time consuming inspection of joints through injection molding, and quickens the manufacturing process.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

Although certain preferred embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of the preferred embodiment.

Figure 1:
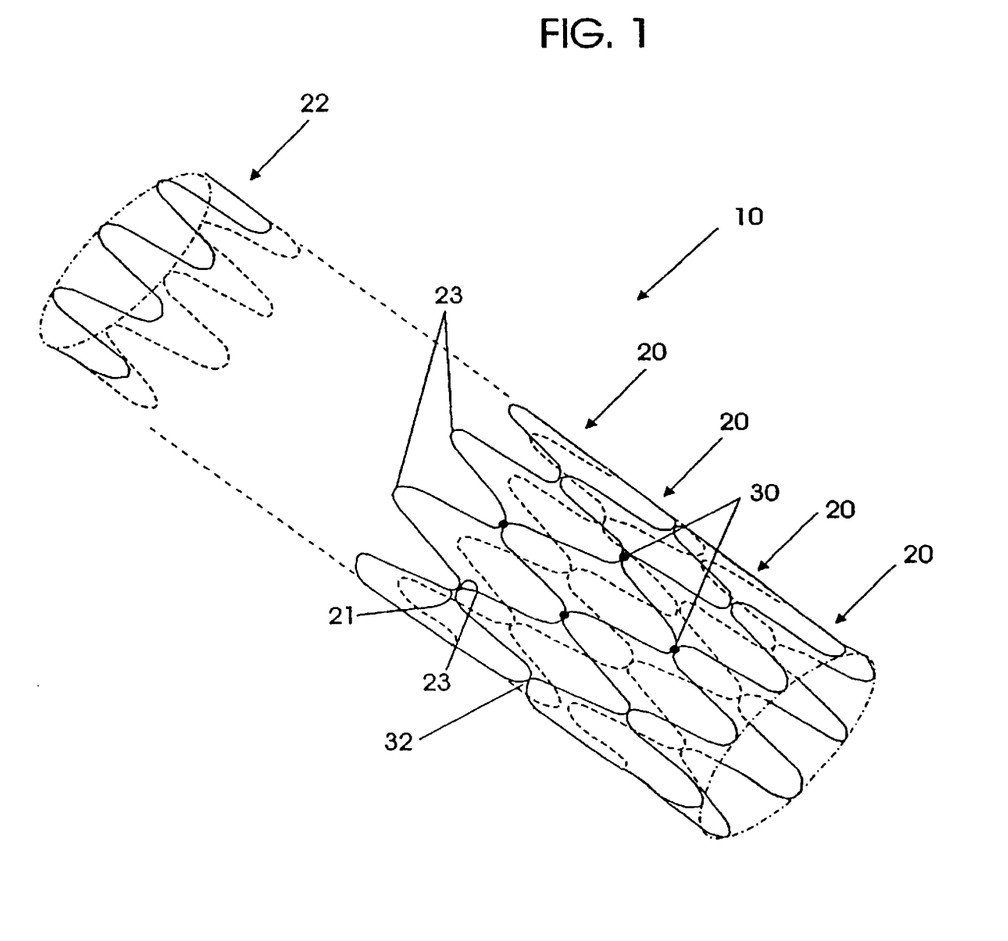
FIG. 1 shows an isometric view of a stent in accordance with a first embodiment of the present invention.
Figure 2:
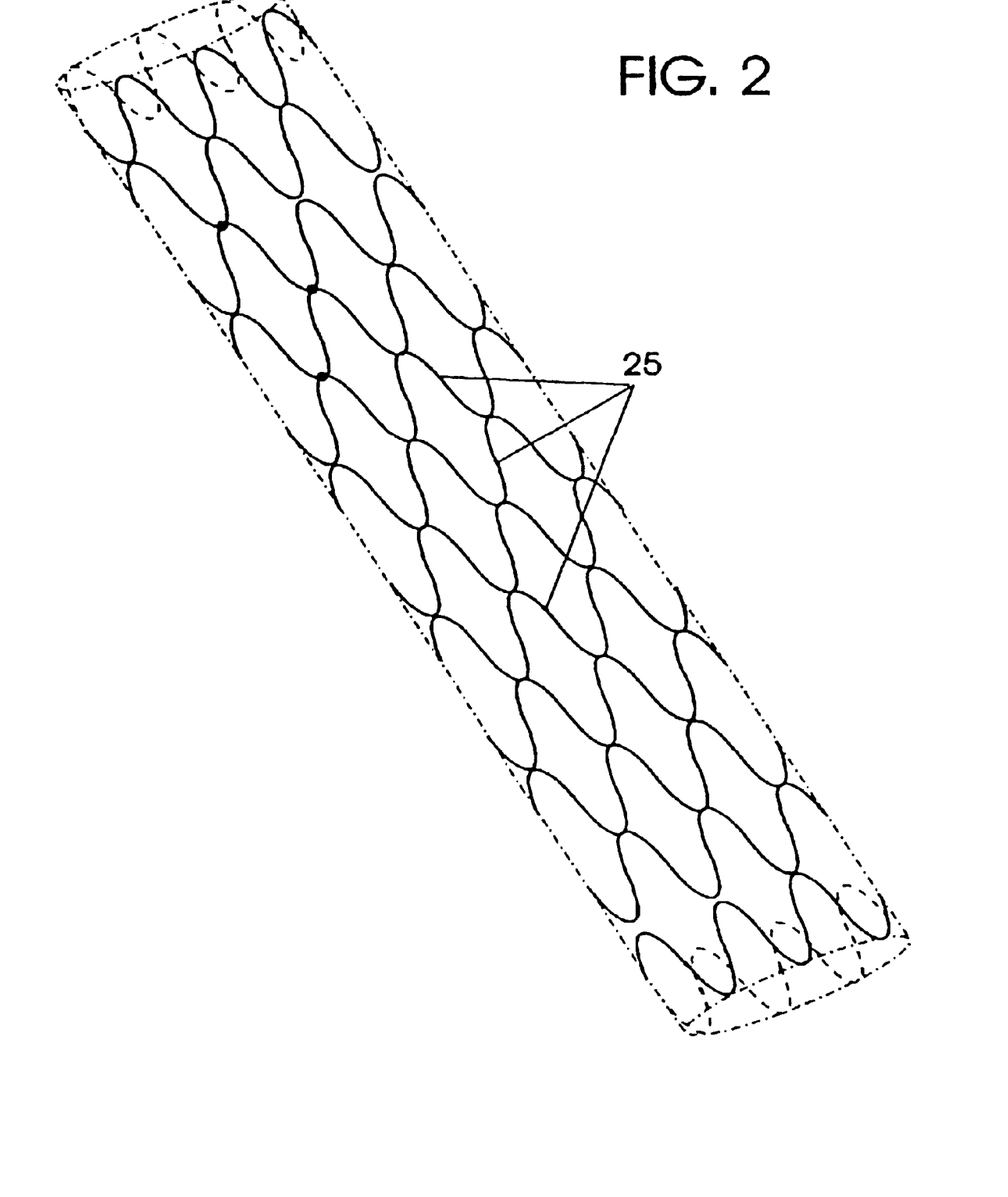
FIG. 2 shows an isometric view of a stent in accordance with a second embodiment of the present invention.

Referring to FIG. 1, a stent 10 in accordance with the present invention is shown. The stent 10 is shown comprising multiple modular, wiring/filament sections 20. In the preferred embodiment, the stent 10 is formed by a series of sections 20 of wire filaments that are endless hoops or bands. However, the stent 10 may also be constructed by a variety of differently shaped filament sections. For instance, a series of lengths of filaments connected along their length (not shown) may be used. Alternatively, as shown in FIG. 2, a piece of filament, not sectional but rather a single length 25, that is looped in a generally helical fashion may be used. It is important to note that all of these structures are hereinafter referred to as "sections" 20 for convenience sake only. Further, the illustration of the sections 20 in the form of hoops is provided to more readily describe the present invention. The use of the term "sections" and the illustrations of hoops are chosen for convenience of illustration and are in no way to be taken as limiting aspects of the claimed invention.

The sections 20 may be made of any material that is relatively stiff but with a high level of allowable plastic deformation. The preferred material is also biocompatible such that it is able to withstand the corrosive environment of the body. For example, tantalum, stainless steel, or a body-compatible polymer such as polyethylene, polytetrafluoroethylene, and polyurethane have been used. The sections 20 may also be made of a biodegradable polymer such as poly (L-lactide). It is also possible to provide the sections 20 with medicinal material incorporated therein to aid in delivery of that material to needed areas. It is also possible to use a combination of the above noted materials, e.g., alternating sections 20 of metal and polymer.

Regardless of the form of the filament (e.g., sections such as hoops or lengths, or helical), the filament must be formed for connection of the filament to itself or an adjacent section 20 such that a structure can be created that is longitudinally flexible for insertion into the artery, yet radially stiff for good artery support. In the preferred embodiment, the sections 20 are in a sinuous shape as illustrated in the drawings. The present invention should not, however, in any way be limited to the sinuous shape illustrated. For example, the sections may be shaped into: a square wave form, a repetitive peak form, etc. Further, the shape need not be identical from section to section or along the length if a single length is chosen, i.e., the frequency of the shape chosen could shift integrally so as to allow for proper alignment and a more dense matting of wire within the stent 10.

As illustrated in FIG. 1, the multiple sections 20 of the preferred embodiment are assembled into a long continuous chain by connecting all or selected crests 21 of one hoop/band to its neighboring hoop's/band's troughs 23. The points of connection being referred to herein as joints 30; the points of a non-connection being labeled 32. The material that forms the joint 30 between sections 20 should be short to ensure axial rigidity. However, the shape of the joint 30 could be varied according to designer requirements. For example, the joint 30 could be shaped like a bar, flat strip, etc. Preferably polyethylene is used.

The joints 30 may be made of a variety of materials. For instance, the joints 30 may be the same material as the sections 20. In a preferred embodiment of the present invention, however, the sections 20 are made of a metal, e.g., tantalum or stainless steel, while the joints are made of either a metal or a polymer. If a polymer is chosen, the polymer may be any body-compatible, material usable in cardiovascular devices such as polyethylene, polytetrafluoroethylene, polyurethane, etc.

As with the sections 20, the joints 30 could also be made from biodegradable polymer such as poly(L-lactide). If made from this biodegradable material, a chain of metal wire band stents 10 could be inserted in the weak artery, become attached to the lining of the artery in two weeks, and a joint 30 would disintegrate having performed a primary function of forming temporary links during initial implantation into the weak artery. As with the sections 20, the joints 30 could also be made of medicinal material to aid in delivery of medication to a needed area.

Figures 3, 3A, 3B:
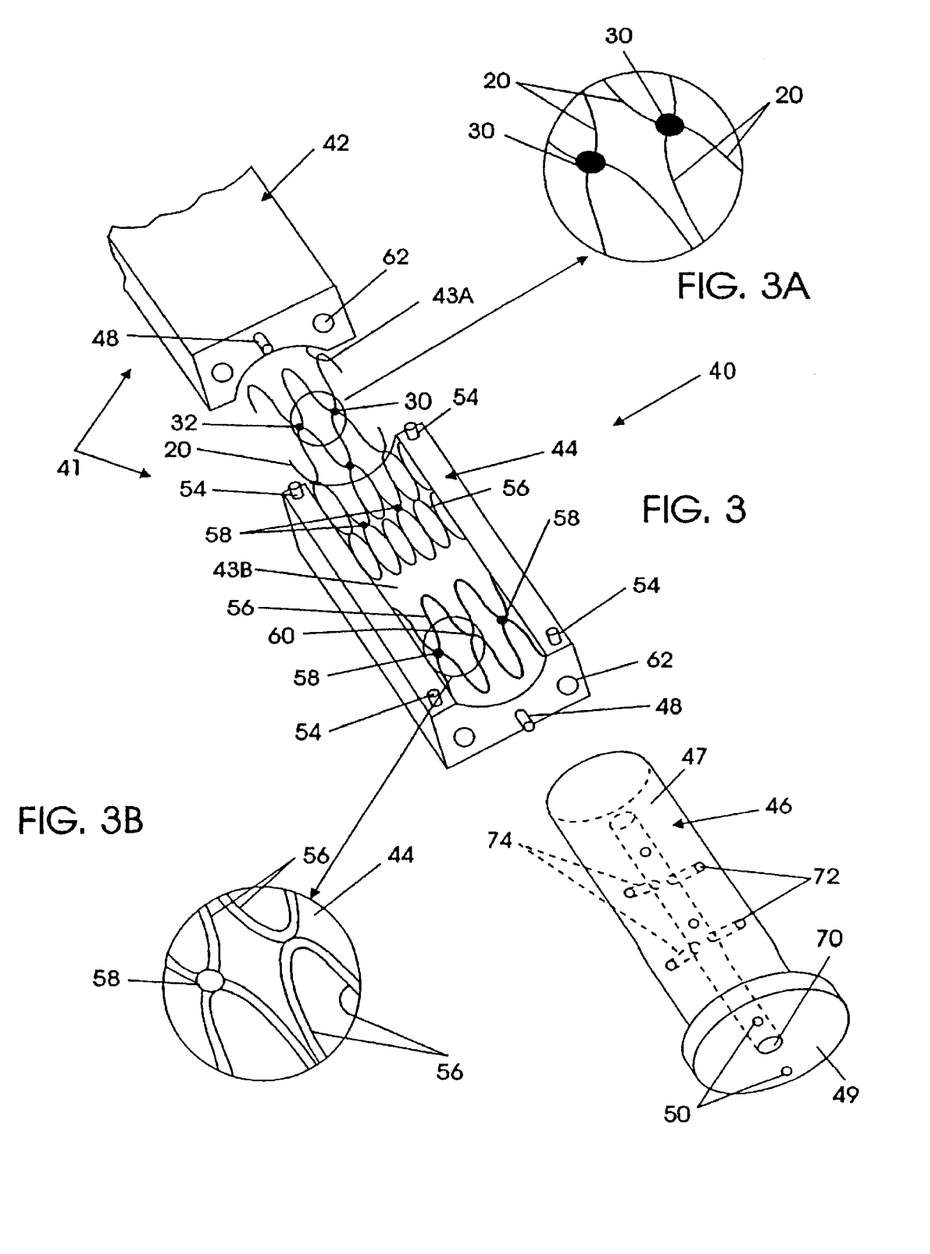
FIGS. 3 and 3B show an isometric and enlarged view of a mold in accordance with a first embodiment of the present invention.
FIG. 3A shows an enlarged view of a portion of the stent in accordance with the first embodiment of the present invention.
Figure 4:
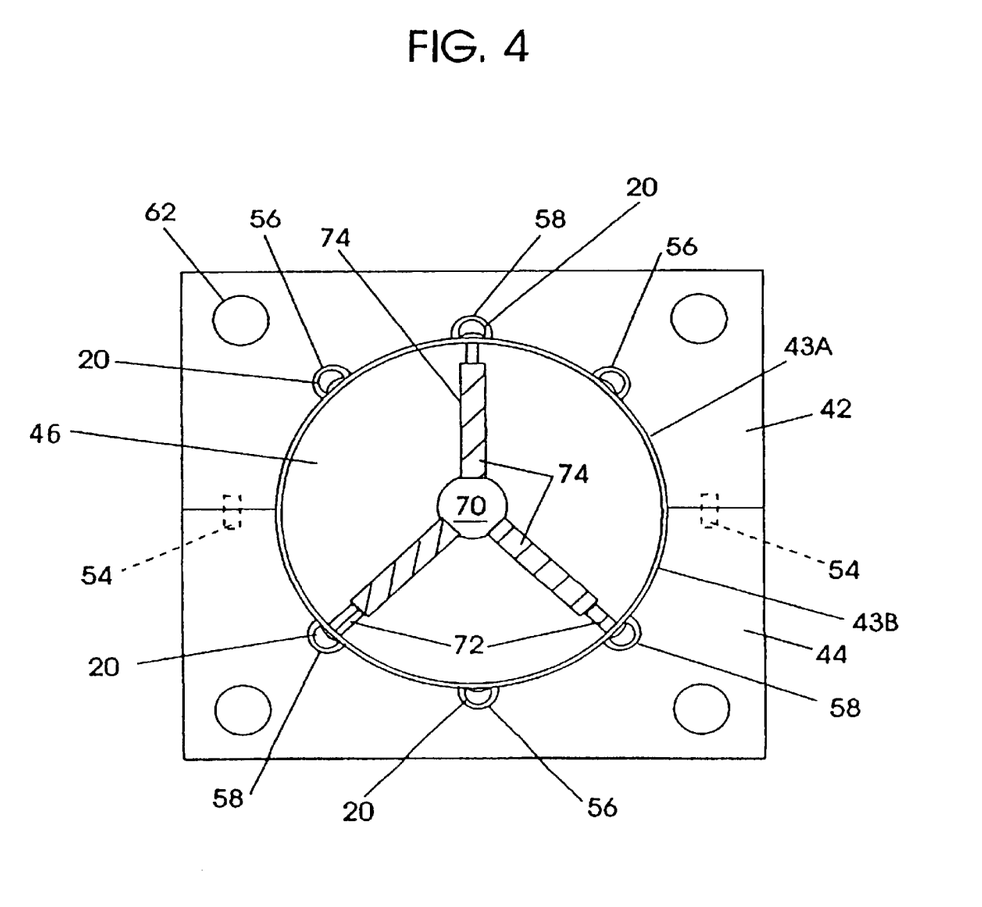
FIG. 4 shows a cross-sectional view of the mold in accordance with the first embodiment of the present invention.

The tooling to create the above described stent 10 is shown in FIGS. 3–6. In FIGS. 3 and 4, a first embodiment of the tooling for use with injection molding processes is shown. The first embodiment includes tooling 40 having a first part in the form of a fixture 41 including a first upper portion 42 and a second lower portion 44, and a second part in the form of a mandrel 46. Each portion 42, 44 of the fixture 41 includes a generally semicylindrical surface 43A and 43B, respectively, which when the portions 42, 44 are mated together form a generally cylindrical interior surface that dictates the shape of the stent 10. It is important to note, however, that the cylindrical shape used herein is only meant to be illustrative as other shapes could be used depending on the particular body cavity in which the stent 10 is to be used. For instance, the shape could be polygonal or elliptical. The upper portion 42 and lower portion 44 are aligned by guide pins 54.

As shown in FIGS. 3 and 3B, each area 43A, 43B includes grooves 56 which are machined into the portions 42, 44 to accommodate the sections 20 of the stent 10. Alternatively, the grooves 56 could also be machined to accommodate a single length of filament 25 if such construction is desired. In any regard, the grooves 56 are positioned to locate the filament, i.e., sections 20, in a desired location for connection into a stent 10. Further, the grooves 56 will most often, but not necessarily, be machined to hold the filament in the shape into which it was originally shaped, e.g., sinuous, thus allowing for ease of insertion of the wiring into the grooves 56.

In order to provide the joints 30 that connect the sections 20, joining openings 58 are machined into the grooves 56 as required. The joining openings 58 are positioned such that molten material injected therein will solidify around adjacent parts of the filament, e.g., the crests 21 and neighboring troughs 23 of sections 20, so as to join them together. The joining openings 58 may be machined to provide any of the before mentioned shapes of joints 30.

Turning to the second part, the mandrel 46 generally includes a body 47 and base 49. The body 47 is generally shaped to closely mate with the internal surfaces 43A, 43B provided between the upper and lower portions 42, 44 of the fixture, i.e., cylindrical. The base 49 tops the mandrel and aids in proper alignment of the mandrel 46 within the internal surfaces 43A, 43B via guide pins 48 in the portions 42, 44 and guide holes 50 in the base 49.

The mandrel 46 provides hot injection material to the joining openings 58 through a series of conduits in the mandrel. In particular, the conduits include an input 70 that enters the base 49 and runs through the center of the body 47, runners 74 which branch off of the input 70, and gates 72 that connect the runners 74 to the joining openings 58. The alignment and close tolerances of the mandrel 46 and fixture inner surfaces 43A, 43B are critical parameters for a successful set of tooling. The mandrel 46 should be made from insulating material, such as ceramic or phenolic, for safe operation. Water cooling may also be provided to the tooling 40 via conduits 62, if necessary.

As an alternative design, the tooling 40 is used as a mold for the overall creation of the stent 10. In this application, the tooling 40 would not receive previously constructed wiring/ filament sections 20 but rather would receive molten material through mandrel 46. The molten material would flow from the mandrel conduits 70, 72, 74 through the joining openings 58 and into grooves 56 thus forming a one piece unitary stent 10 upon hardening. In this situation, it may be necessary to make certain modifications in the tooling 40 that would accommodate more fluid flow. For instance, more runners 74 and gates 72 may be necessary within the mandrel 46.

The process of creating a stent 10 using the non-injection molding tooling is as follows. First, the wiring is shaped, e.g., into a sinuous section 20. Second, the section 20 is placed within the grooves 56. The placing of the sections 20 may occur in a variety of ways. For instance, one of the sections 20 may be placed in one of the portions 42, 44 or the sections may be placed over the mandrel 46 and the mandrel positioned over one of the portions 42, 44. Third, the tooling 40 is enclosed by coupling the missing part, i.e., portion 42, 44 or the mandrel 46. Fourth, joints 30 are formed by the insertion of molten material into the mandrel 46 that flows to the joining openings 58 and solidifies. Lastly, the tooling is opened and the completed stent 10 is removed from the tooling 40 for use.

In the alternative that the tooling 40 is used as a complete mold, the first two steps above are omitted. The tooling is connected, the molten material is injected and the completed stent 10 is removed from the tooling once the material is hardened.

Figure 5:
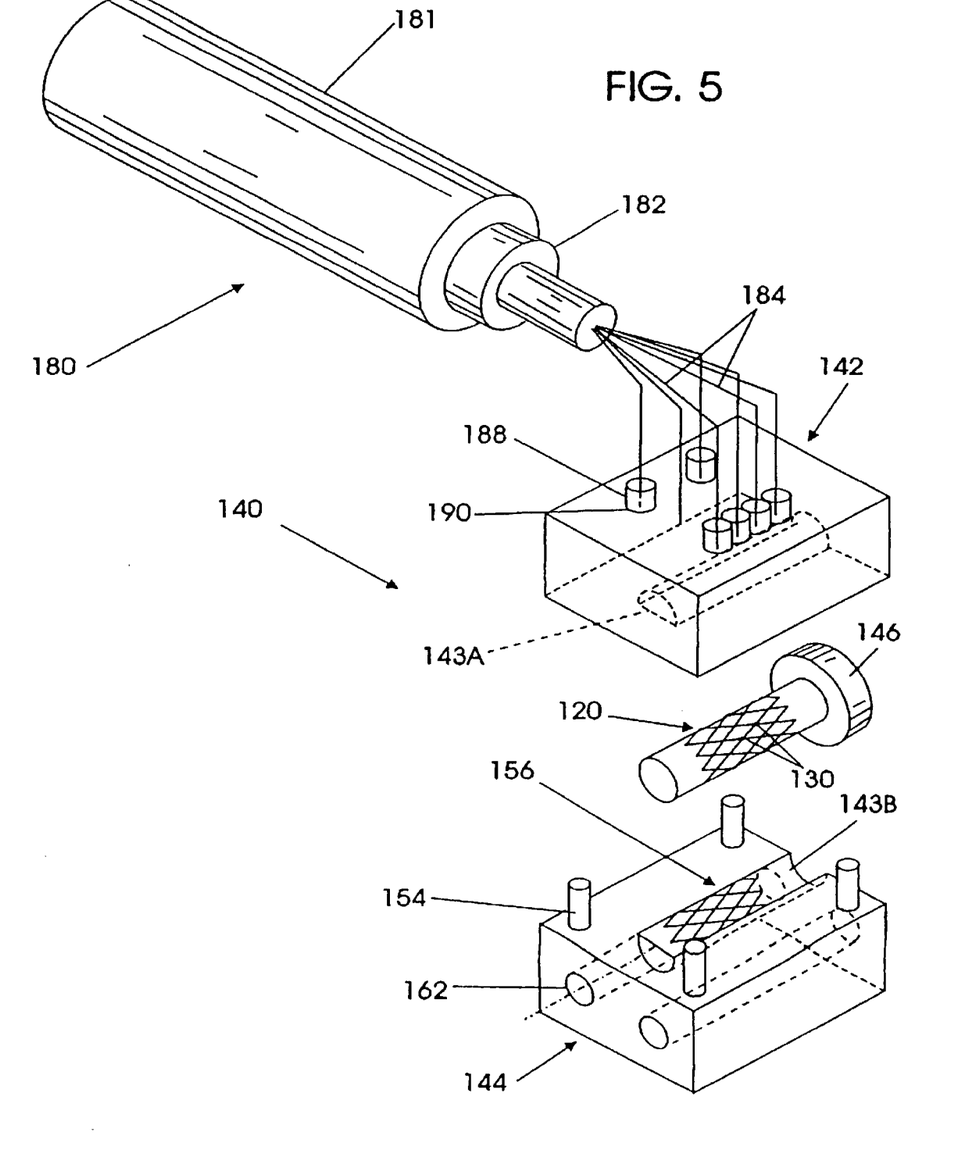
FIG. 5 shows an isometric view of a mold in accordance with a second embodiment of the present invention.
Figure 6:
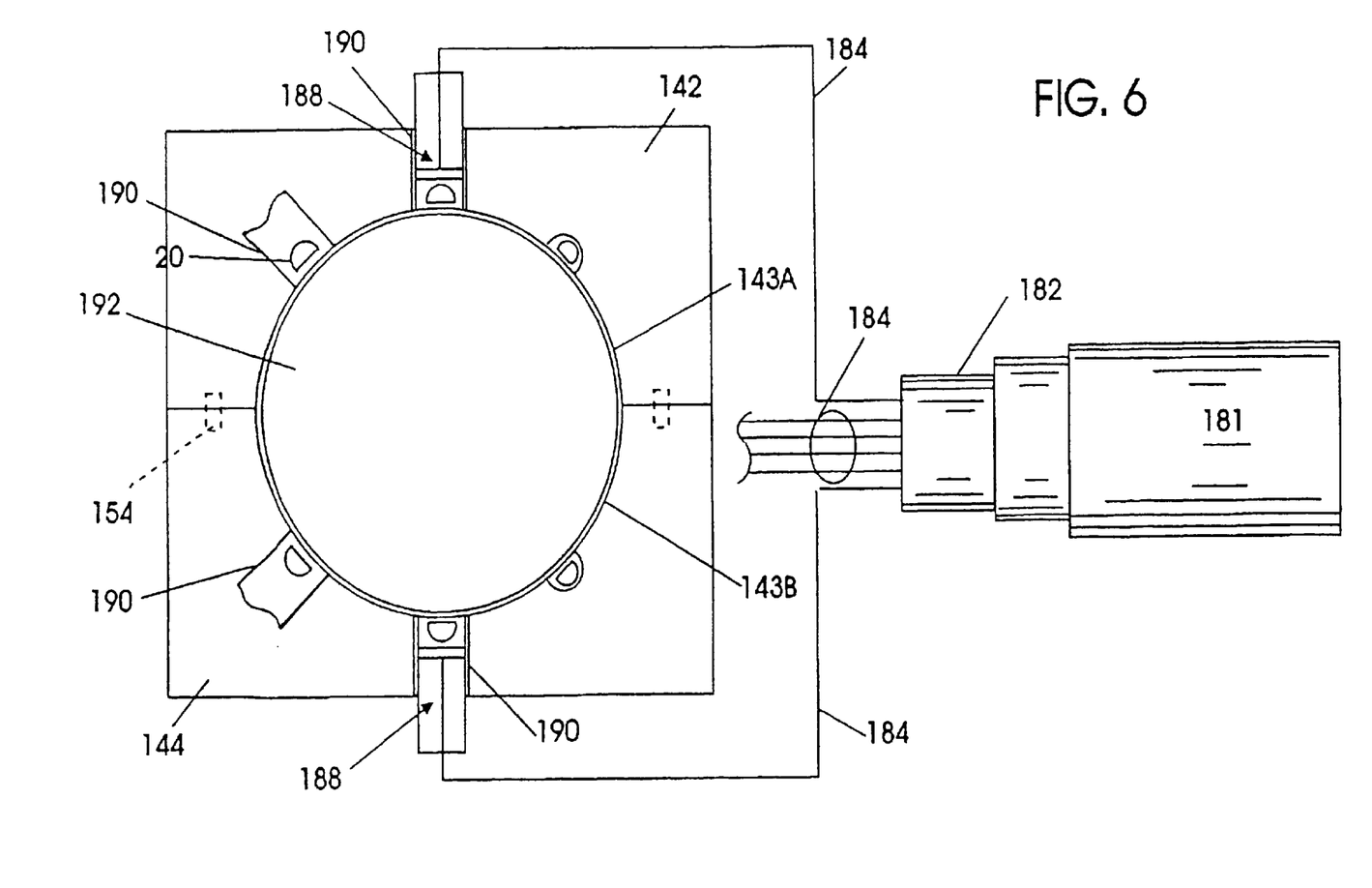
FIG. 6 shows a cross-sectional view of the mold in accordance with the second embodiment of the present invention.
Figure 7:
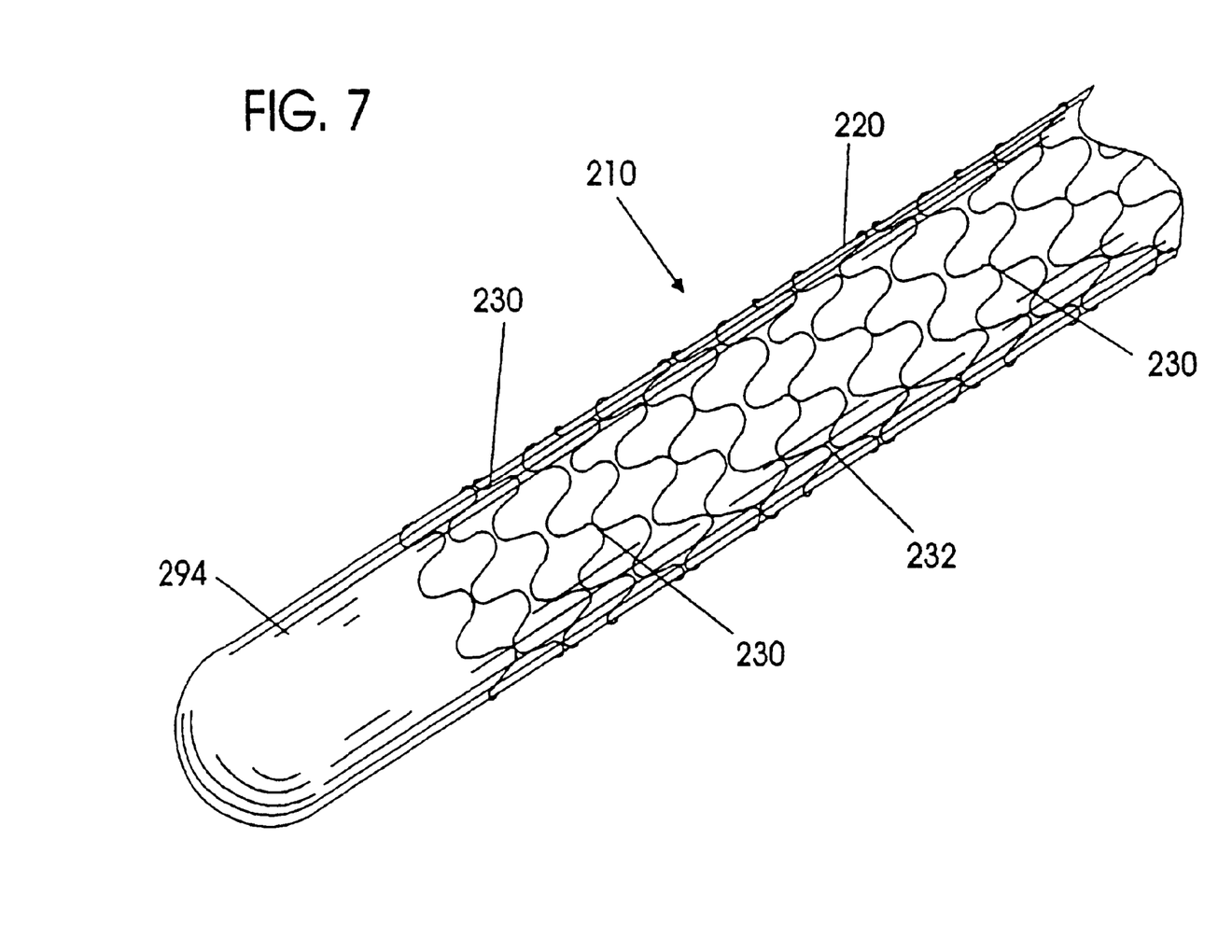
FIG. 7 shows an isometric view of a stent in combination with an angioplasty balloon in accordance with the present invention.

Referring to FIGS. 5 and 6, a second embodiment of the tooling in accordance with the present invention is shown. This tooling allows for uniform, one time welding of stent sections 120. The one time welding is provided by a laser and fiber optic system 180.

The second embodiment is similar in structure to that of the first embodiment in that the tooling 140 includes a first part having a first upper portion 142 and a lower second portion 144. The portions 142, 144 each have a generally semicylindrical surface 143A, 143B which join to form a generally cylindrical interior surface. A mandrel 146 is provided to support the sections 120 within the tooling 140. Again, it is important to note that the shape of the surfaces 143A, 143B and mandrel 146 may be varied, e.g., polygonal or elliptical.

In this embodiment, however, the mandrel does not have conduits therein. Here, the portions 142, 144 are provided with a plurality of fiber optic channels 190 that open onto the grooves 156 at desired joint positions, e.g., where filaments of neighboring sections 120 are adjacent one another. Within each channel 190, a fiber optic lens 188 is positioned. The lenses 188 are connected via fiber optic lines 184 to a heating source 181, e.g., a laser. The laser heating source 181 is a source of welding heat that is transmitted along the fiber optic lines 184 and focused by lenses 188 on the selected points of the sections 120.

With the present invention, the repetitive heating and cooling of the sections 120 during welding is reduced in that all of the joints 30, 130 are created in a single step, i.e., a material injection or a single transmission from a heating source 181 to lenses 188. As a result, the manufacturing process is quicker and more reliable using the present invention because of the substantially simultaneous creation of the joints 30, 130. Furthermore, the tooling 40, 140 allows for more consistent alignment of the joints 30, 130 because the sections 20, 120 are held in their desired position. The stent created, therefore, has maximum flexibility for insertion with maximum rigidity for artery wall support.

FIG. 6 shows a stent 210 in combination with an angioplasty balloon 294. The device is shown in an intermediate step of use in which an angioplasty balloon 294 is enlarged within the stent 210. The stent 210 may take the form of any of the above-identified stent embodiments, e.g., filaments formed of a first material and the joints 230 of a second material. In use, the angioplasty balloon 294 and stent 210 are used together to position the stent 210 within an artery of a body. In particular, the stent 210 is collapsed around the balloon 294 and then positioned within a body artery where the balloon 294 is expanded to extend the stent 210 to an in-use position. Accordingly, the present invention also includes the angioplasty balloon 294 and stent 210 in combination.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A method of making a stent, the method comprising the steps of:

providing a fixture having internal grooves;

placing filaments into the grooves; and providing a mandrel having conduits to deliver joint forming material to the grooves to join the filaments together at spaced points.

2. The method of claim 1, wherein the step of providing a fixture having internal grooves includes providing the grooves in a generally cylindrical shape.

3. The method of claim 1, wherein the step of joining the filaments includes injecting a molten material to form joints between the filaments.

4. The method of claim 1, wherein the step of providing a fixture includes providing a mold with a generally cylindrical interior surface.

5. The method of claim 4, wherein the grooves include openings to receive the joint forming material.

6. The method of claim 1, wherein the step of placing the filaments into the grooves includes placing the filaments such that portions of the filaments are proximate one another.

* * * * *